(12) United States Patent
Calderon

(10) Patent No.: US 8,454,626 B2
(45) Date of Patent: Jun. 4, 2013

(54) HYSTERECTOMY RING

(76) Inventor: Ilan Calderon, HaGlilit (IL)

( * ) Notice: Subject to any disclaimer, the term of this patent is extended or adjusted under 35 U.S.C. 154(b) by 366 days.

(21) Appl. No.: 12/673,496

(22) PCT Filed: Jun. 19, 2008

(86) PCT No.: PCT/IL2008/000840
§ 371 (c)(1),
(2), (4) Date: Feb. 14, 2010

(87) PCT Pub. No.: WO2009/022326
PCT Pub. Date: Feb. 19, 2009

(65) Prior Publication Data
US 2011/0190783 A1    Aug. 4, 2011

(51) Int. Cl.
*A61B 17/42*    (2006.01)
(52) U.S. Cl.
USPC ........................................... 606/119; 600/591

(58) Field of Classification Search
USPC ... 606/118, 119, 157, 174; 128/898; 600/587, 600/588, 591
See application file for complete search history.

(56) References Cited

U.S. PATENT DOCUMENTS

| 4,085,756 | A |   | 4/1978 | Weaver |
| 5,108,408 | A |   | 4/1992 | Lally |
| 5,709,679 | A | * | 1/1998 | Essig et al. ...................... 606/46 |
| 5,807,281 | A | * | 9/1998 | Welch ........................... 600/588 |
| 2004/0092847 | A1 |   | 5/2004 | Welch |

* cited by examiner

*Primary Examiner* — Victor Nguyen
(74) *Attorney, Agent, or Firm* — Dekel Patent Ltd.; David Klein

(57) ABSTRACT

A device including a ring for placing at an interface between a vagina and a uterus, the ring including an annular tube with a hollow annular track with an aperture formed in the ring that communicates with the annular track, and fixation elements for maintaining the ring in place in the vagina.

4 Claims, 3 Drawing Sheets

HYSTERECTOMY RING

CROSS-REFERENCE TO RELATED APPLICATIONS

This application claims priority under 35 USC §119 to U.S. Provisional Patent Application Ser. No. 60/955,877, filed Aug. 15, 2007.

FIELD OF THE INVENTION

The present invention relates to a device for performing a hysterectomy.

BACKGROUND OF THE INVENTION

A typical abdominal hysterectomy involves making an incision in the abdominal wall and underlying peritoneum so as to expose the abdominal cavity and the various organs therein including the uterus. Laparoscopic hysterectomy involves a smaller incision. The uterus is removed at its cervical juncture with the vagina, commonly referred to as the fornix. Upon identifying this juncture, surrounding blood vessels are ligated and circumcision is made about the vaginal wall at the fornix area. Upon removal of the uterus, the resulting vaginal edges are sewn shut.

Various problems arise in this general operation. The exact location of the vaginal fornix may be difficult to find in some patients. Moreover, constant attention must be made to bleeding due to the surrounding ligaments and blood vessels. Also, a clean, circular incision about the vaginal wall at the fornix may be difficult.

U.S. Pat. No. 5,108,408 to Lally describes a surgical tool for use in abdominal hysterectomies, which includes an inner uterine-ring assembly having a ring for insertion into the vagina at the juncture of the cervix and vagina. An outer clamping assembly insertable through a surgically opened abdominal cavity is clamped about the inner ring with the vaginal tissue interposed therebetween. The combination presents a scalpel guide for surgical circumcision of the interposed tissue as well as controls undesirable bleeding from the circumcised tissue.

SUMMARY OF THE INVENTION

The present invention seeks to provide a surgical device for performing a hysterectomy, as is described more in detail hereinbelow. In accordance with an embodiment of the present invention, the device includes a ring for placing at the interface between the vagina and the uterus. The ring has an annular slot or track for placing therein a ball tip diathermy electrode. The electrode is used to cut and separate the uterine cervix from the vagina during an open or laparoscopic hysterectomy. The ring has peripheral fingers to maintain the ring in place in the vagina.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1A:
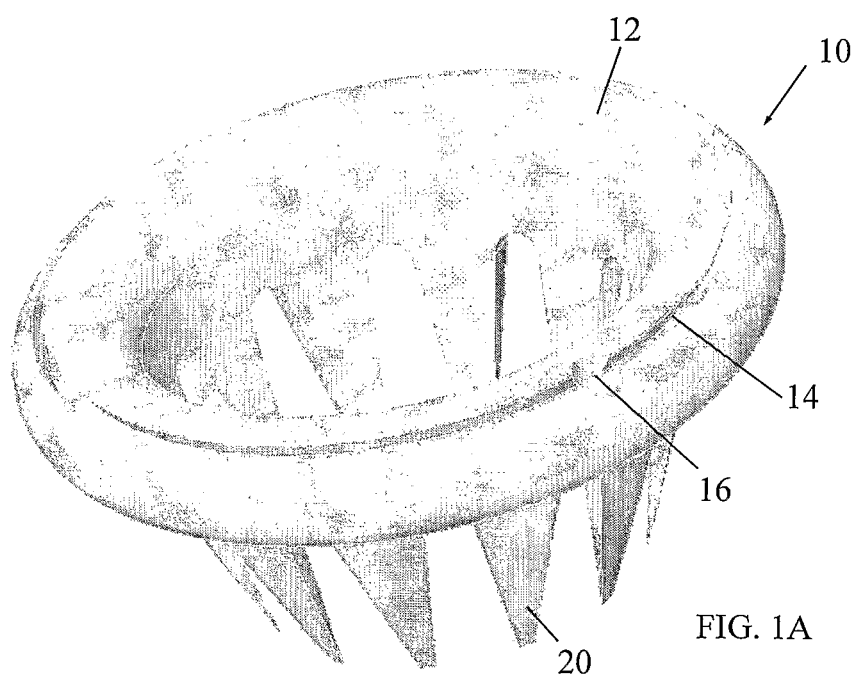
FIGS. 1A and 1B are simplified pictorial and partially cutaway illustrations, respectively, of a surgical device for performing a hysterectomy, constructed and operative in accordance with an embodiment of the present invention.
Figure 1B:
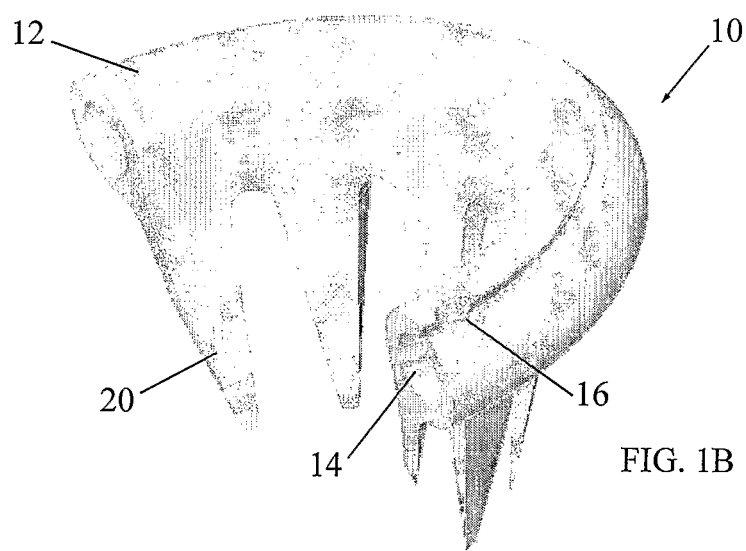

Reference is now made to FIGS. 1A and 1B, which illustrate a surgical device 10 for performing a hysterectomy, constructed and operative in accordance with an embodiment of the present invention.

Figure 2:
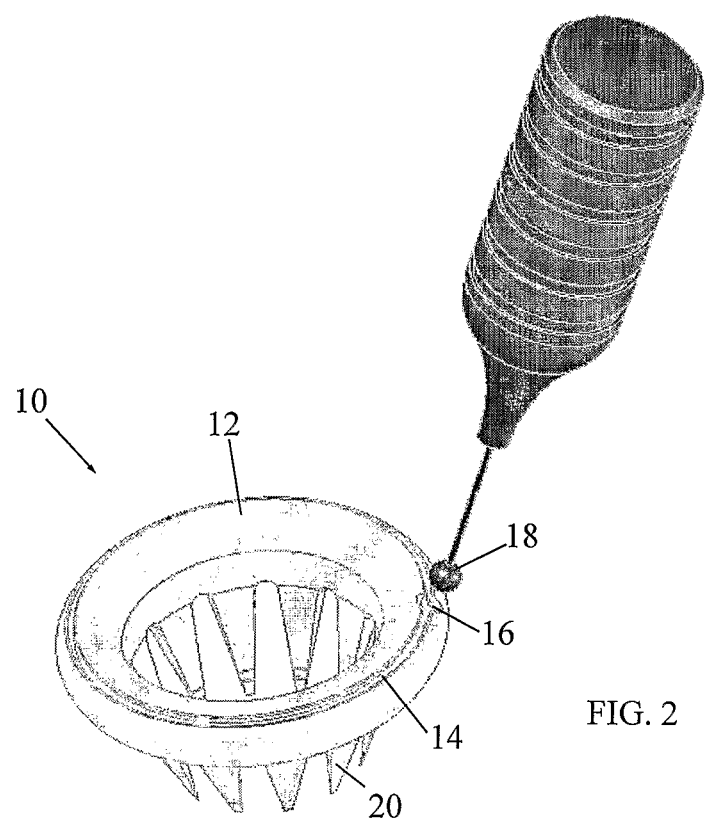
FIG. 2 is a simplified pictorial illustration of the surgical device of FIGS. 1A and 1B, shown with a diathermy electrode device for performing hysterectomy.

Device 10 may include a ring 12 for placing at the interface between the vagina and the uterus. Ring 12 may be constructed of a medically safe metal, such as stainless steel AISI 316L, for example. Ring 12 is an annular tube with a hollow annular track 14. An aperture 16 is formed in ring 12 that communicates with annular track 14. Aperture 16 is sized so that a ball tip diathermy electrode 18 (FIG. 2) can be placed therein and moved along annular track 14. The electrode 18 is used to cut and separate the uterine cervix from the vagina during an open or laparoscopic hysterectomy.

As is known in the art, diathermy is a heating effect produced in the body by high-frequency electric current for cutting or coagulating tissue. The frequency may be typically, but not limited to, 0.3 to 5.0 MHz. In the case of the ball tip diathermy electrode 18, the electrode is monopolar. Typically, a large size electrode (e.g., but not necessarily, having an area of 100 cm$^2$) is attached to the skin (not shown) and ball tip diathermy electrode 18 is held in contact with the tissue to be cut or coagulated. This causes intense heating at the point of contact between electrode 18 and the tissue since the current density is very high. Little or no heating is produced at the large electrode because the current density is low.

In one embodiment, the ball tip of diathermy electrode 18 protrudes from annular track 14 to contact the uterine cervix tissue to cause the incision. In another embodiment, the ball tip of diathermy electrode 18 is fully received in annular track 14 and generates heat by conduction through the outer surface of ring 12, which contacts the uterine cervix tissue and causes the incision.

Fixation elements 20 are provided to help maintain ring 12 in place in the vagina. In accordance with an embodiment of the present invention, the fixation elements 20 include a plurality of resilient peripheral fingers that extend from ring 12 (e.g., in a direction opposite to aperture 16).

At the beginning of the hysterectomy procedure, the surgeon inserts device 10 through the vagina, around the uterine cervix, in order to separate the uterine cervix from the vagina. The surgeon then inserts the tip of diathermy electrode 18 into annular track 14 and moves the electrode 18 in track 14 to make an incision around the uterine cervix at the interface between the vagina and the uterus. The device 10 is distinguished by its simplicity, ease of use and safety.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:
1. A device comprising:
   a ring for placing at an interface between a vagina and a uterus, said ring comprising an annular tube with a hollow annular track with an aperture formed in said ring that communicates with said annular track;

fixation elements for maintaining said ring in place in the vagina; and a ball tip diathermy electrode placed through said aperture into said annular track, wherein said aperture is annular and parallel to an annular centerline of said hollow annular track.

2. The device according to claim 1, wherein said fixation elements comprise a plurality of resilient peripheral fingers that extend from said ring.

3. The device according to claim 2, wherein said resilient peripheral fingers extend from said ring in a direction opposite to said aperture.

4. A method comprising:

placing a device at an interface between a vagina and a uterus, said device comprising a ring that includes an annular tube with a hollow annular track with an aperture formed in said ring that communicates with said annular track, and fixation elements for maintaining said ring in place in the vagina; and inserting a tip of a diathermy electrode into said annular track and moving said diathermy electrode to make an incision at the interface between the vagina and the uterus, wherein said aperture is annular and parallel to an annular centerline of said hollow annular track.

* * * * *